US00PP10474P

United States Patent [19]

Bloom

[11] Patent Number: Plant 10,474

[45] Date of Patent: Jun. 30, 1998

[54] GERANIUM PLANT NAMED BRESSINGHAM'S DELIGHT

[75] Inventor: Adrian Bloom, Norfolk, England

[73] Assignee: Blooms of Bressingham Ltd., Norfolk, England

[21] Appl. No.: 794,059

[22] Filed: Feb. 4, 1997

[51] Int. Cl.[6] ..... A01H 5/00

[52] U.S. Cl. ..... Plt./87.12

[58] Field of Search ..... Plt./87.12

*Primary Examiner*—James R. Feyrer

*Attorney, Agent, or Firm*—Foley & Lardner

[57] ABSTRACT

A new and distinct cultivar of Geranium plant named 'Bressingham's Delight', characterized by its dark pink flowers, profuse flowering, vigorous yet relatively low growth habit, and its long flowering period beginning in mid-April and continuing into late October.

1 Drawing Sheet

The present invention relates to a new and distinct cultivar of hardy perennial herbaceous plant of the genus Geranium, a member of the Geraniaceae family, and known by the cultivar name 'Bressingham's Delight'.

This new cultivar was discovered by its inventor Adrian Bloom as a seedling among several Geraniums on the premises of Finest Quality Plants, a subsidiary company of Blooms of Bressingham Ltd. located in Holland. The plant was brought back to England for further assessment and propagation at Bressingham, Diss, Norfolk, England. The seed parent was a presently unknown cultivar of the genus, and the pollen or male parent was a presently unknown cultivar of *Geranium oxonianum,* with the latter in turn being a cross between *Geranium endressii* and *Geranium versicolor.* The new cultivar was recognized primarily due to its vigorous yet relatively low flowering height and its long flowering period.

Subsequent asexual reproduction by the inventor by leaf cuttings taken in Bressingham, England, established that the unique combination of characteristics as herein disclaimed for the new cultivar are fixed and retained through successive generations of asexual reproduction.

The new cultivar has not been observed under all possible environmental conditions. The phenotype may vary with variations in environment such as temperature, light intensity without, however, any variance in the genotype.

The following traits have been repeatedly observed and are determined to be basic characteristics of the new cultivar, which in combination distinguish the new cultivar from others:

1. Its bushy clump habit produces profuse and continuous flowering in England from mid-April through late October.
2. Dark pink flowers with prominent veins.
3. Palmately divided fresh green leaves make a pleasing backdrop to abundant, veined pink flowers.
4. The plant thrives best in full sun and well drained soil but can also be grown in shade under dry conditions. The new cultivar is ideal for use in borders and containers.
5. Vigorous yet relatively low growth and flowering habit.
6. The flowers have a classic "crane's bill" shape which characterizes the genus.

In comparison to 'Wargrave Pink' (*G.×oxonianum*), perhaps the closest cultivar for comparison purposes, 'Bressingham's Delight' is generally similar in habit and flower color. However, 'Bressingham's Delight' has move vigorous growth while maintaining a low flowering height, is a more profuse bloomer, and has a longer flowering period.

The color photograph comprises a top perspective view of plants of the new cultivar growing in a border setting, illustrating the general quality and color of the flowers and foliage.

The following is a detailed description of the new cultivar based on plants grown in Bressingham, England. All color determinations are based on The Royal Horticultural Society Colour Chart.

Plant:

*Origin.*—Seedling selection from Geranium×*G. oxonianum.*

*Type.*—Herbaceous perennial.

*Habit.*—Clump forming.

*Size.*—Mature plants are 40 cm in height with a spread of 60 cm.

*Root system.*—Fibrous.

*Plant vigor.*—A perennial that shows vigorous and healthy growth throughout Great Britain.

*Blooming habit.*—Showy dark pink flowers are borne on a spreading raceme from a flower stem arising at the base of the plant.

*Blooming period.*—From April continuing into late October.

*Hardiness.*—Winter hardy throughout the British Isles. The plant has not been fully tested for maximum summer tolerance above 32° C. (90° F.).

Flowers:

*Petals.*—Five veined petals of equal size.

*Flower shape.*—Funnel shaped. The petals curl back as the flowers age. The veins show up strongly in new flowers. A silvery sheen can also be seen.

*Flower type.*—Compound, each petal curls back on itself.

*Flower size.*—3 cm in diameter.

*Carpels.*—5 celled.

*Stamens.*—Small. Pale pink.

*Color.*—The petals of mature flowers are approximately 62A to 63B–D.

Foliage:

*Arrangement.*—Petiole arising from base of plant bearing deeply cut, compound leaves.

*Texture.*—Both upper and lower surfaces are hairy.

*Length.*—6–8 cm.

*Width.*—8 cm.

*Petiole length.*—8–20 cm.

*Margins.*—Parted.

*Apex.*—Acute.

*Base.*—Sagittate.

*Color.*—Mature leaves, upper surface 137A, under surface 137B.

I claim:

1. A new and distinct cultivar of Geranium plant named 'Bressingham's Delight', as shown and described.

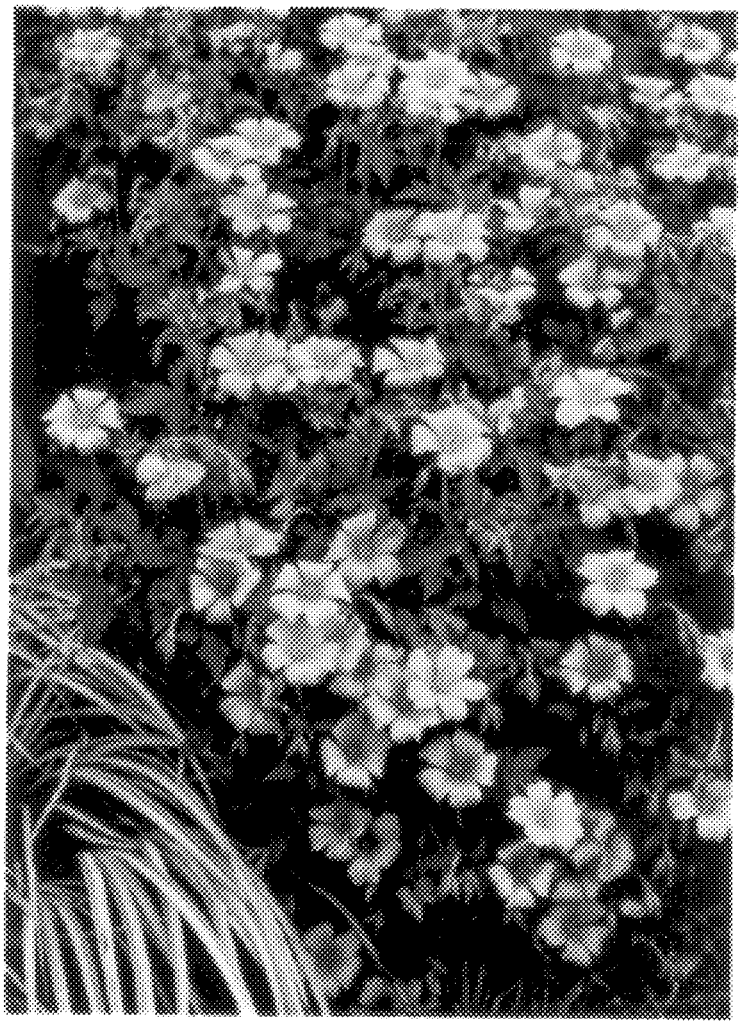

* * * * *